United States Patent [19]
Satake et al.

[11] Patent Number: 6,097,493
[45] Date of Patent: Aug. 1, 2000

[54] DEVICE FOR EVALUATING QUALITY OF GRANULAR OBJECTS

[75] Inventors: Satoru Satake, Tokyo; Yasuharu Mitoma, Hiroshima, both of Japan

[73] Assignee: Satake Corporation, Tokyo, Japan

[21] Appl. No.: 09/323,931

[22] Filed: Jun. 2, 1999

[30] Foreign Application Priority Data

| Jun. 2, 1998 | [JP] | Japan | 10-152641 |
| Feb. 9, 1999 | [JP] | Japan | 11-030784 |

[51] Int. Cl.$^7$ .............. G01B 11/04; B07C 5/342
[52] U.S. Cl. ............ 356/376; 356/239.1; 209/580; 209/587
[58] Field of Search ............ 356/237.1, 239.1, 356/376; 209/587, 939, 639, 585, 576, 577, 580, 581; 348/91, 132; 250/223 R, 559.01

[56] References Cited

U.S. PATENT DOCUMENTS

| 4,371,081 | 2/1983 | Satake | 209/580 |
| 4,630,736 | 12/1986 | Maughan et al. . | |
| 4,699,274 | 10/1987 | Saika | 209/587 |
| 5,135,114 | 8/1992 | Satake et al. . | |
| 5,148,923 | 9/1992 | Fraenkel et al. | 209/539 |
| 5,220,400 | 6/1993 | Anderson et al. . | |
| 5,443,164 | 8/1995 | Walsh et al. | 209/587 |
| 5,638,961 | 6/1997 | Satake et al. | 209/580 |
| 5,669,511 | 9/1997 | Satake et al. | 209/580 |
| 5,735,402 | 4/1998 | Pezzoli et al. | 209/577 |

FOREIGN PATENT DOCUMENTS

| 0 443 769 | 8/1991 | European Pat. Off. . |
| 0 727 260 | 8/1996 | European Pat. Off. . |

*Primary Examiner*—Hoa Q. Pham
*Attorney, Agent, or Firm*—Fish & Richardson, P.C.

[57] ABSTRACT

A granular object evaluation device for evaluating quality and shapes of transparent or translucent granular objects includes an illuminating device for irradiating light to the object fed into a measuring area by a feeder, a detecting device in which a detection viewing line is directed to the measuring area through a center portion of the illuminating device and which receives reflection light from the object, a light shielding plate located between the illuminating device and the detecting device, for preventing the light from the illuminating device from directly incident on the detecting device, and having an opening through which the detection viewing line passes, and a control device for analyzing detected signals from the detecting device and evaluating quality and shapes of the granular object. The device further includes a shielding mask for shielding light from a predetermined area such that no irradiation is made directly on the granular object from the predetermined area of the illuminating device with the detection viewing line as the center. Evaluation of quality of the granular object can be effected without being influenced by the reflection light which affects in the evaluation of the quality as an obstacle.

6 Claims, 7 Drawing Sheets

DEVICE FOR EVALUATING QUALITY OF GRANULAR OBJECTS

BACKGROUND OF THE INVENTION (1) Field of the Invention

The present invention relates to a device for evaluating quality of granular objects including transparent or translucent pellets and rice grains, and more particularly to a device which, with respect to granular objects to which the reflection light dependent on the shapes of, for example, a pellet, influences the evaluation of the quality affected by, for example, color, enables the accurate evaluation of the shapes and quality without being influenced by the reflection light which affects in the evaluation of the quality as an obstacle.

(2) Description of the Related Art

In the case of evaluating the quality of the transparent pellet, it is known that, when the transparent pellet is irradiated by illumination light from a light source, the reflection light which has nothing to do with the quality evaluation of the transparent pellet is caused to occur from the end faces or deformed surfaces of the pellet and, when this reflection light is received by the light receiving section, the reflection light from the end faces of the pellet is known to be detected as dark light. At the light receiving section, the reflection light detected as dark light cannot be distinguished from the light which is reflected from the colored portion of the transparent pellet and is likewise detected as dark light, resulting in a mis-evaluation.

Figure 1:
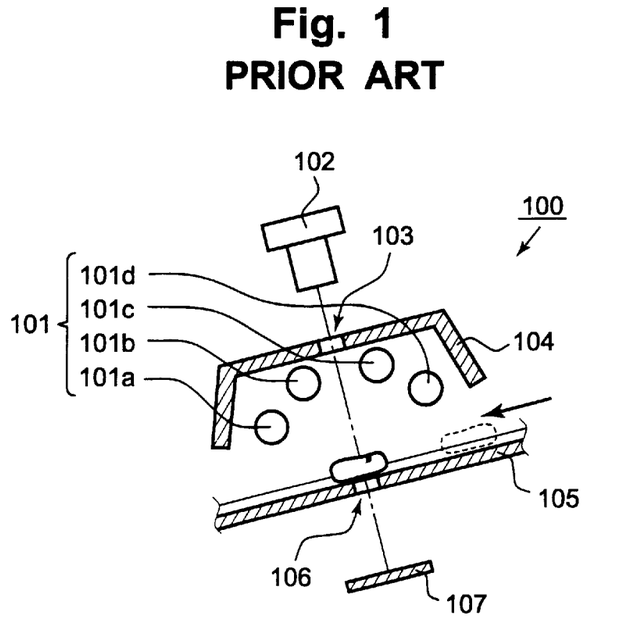
FIG. 1 is a diagram for showing an example of a conventional quality evaluation device.

First, a conventional quality evaluation device 100 shown by FIG. 1 is explained. The device 100 comprises an illumination unit 101 equipped with a plurality of fluorescent lamps 101a–101d which constitute light sources, a light receiving section 102 disposed above the illumination unit, a light shielding plate 104 equipped with an opening 103 which is disposed between the illumination unit 101 and the light receiving section 102 and which passes a viewing line of the light receiving section 102, and a feeding means 105 which feeds granular objects and is disposed with inclination on the viewing line extended from the opening 103 of the light shielding plate 104. On the extended viewing line of the feeding means 105, there is provided a light passing hole 106 and, on the viewing line extended from the light passing hole 106, there is provided a white background 107 as a color reference plate.

Figure 2:
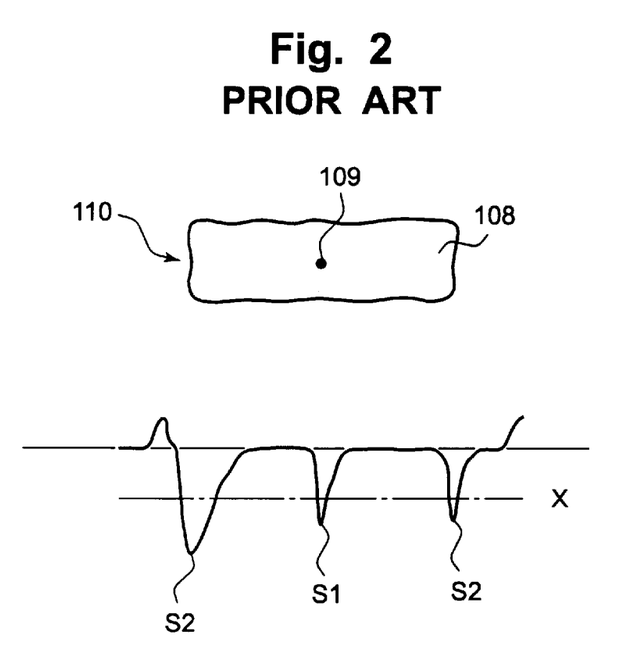
FIG. 2 is a diagram for showing reflection light signals of a transparent pellet in the conventional quality evaluation device.

In the device constructed as above, when a defective pellet having a colored portion is to be sorted from among transparent or translucent pellets, the signal waves as shown in FIG. 2 are obtained from the defective pellet. That is, in the case where the pellet is transparent, the detection is made of a detection signal S2 detected based on the light received as the dark light from both the end faces 110 of the pellet, in addition to a detection signal S1 based on the dark reflection light from the colored portion 109. In this way, from the transparent pellet 108 having a colored portion, the detection is made of the signal S2 and the signal S1 related to the two end faces 110 and the colored portion 109. In order to evaluate the colored portion 109 from changes in these signals, it is necessary to provide a means which distinguishes from each other the signals based on the end faces 110 and that based on the colored portion 109. However, since these signals both represent dark light, whatever different threshold values are set, it will be difficult to distinguish the two different signals. Thus, the evaluation by way of shapes of the transparent pellets or by counting the number of samples was more difficult. Even when the colored portion was detected, the counting of the number of pellets was not possible because the determination of a division of one pellet from another, which is transparent, was unable.

Figure 3:
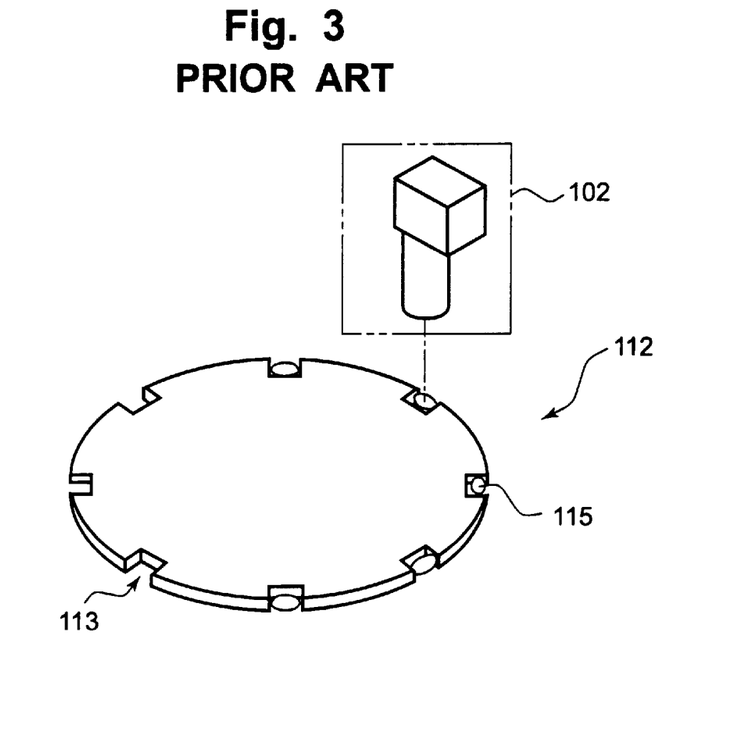
FIG. 3 is a diagram for showing a feeding means for grains in the conventional quality evaluation device.
Figure 4:
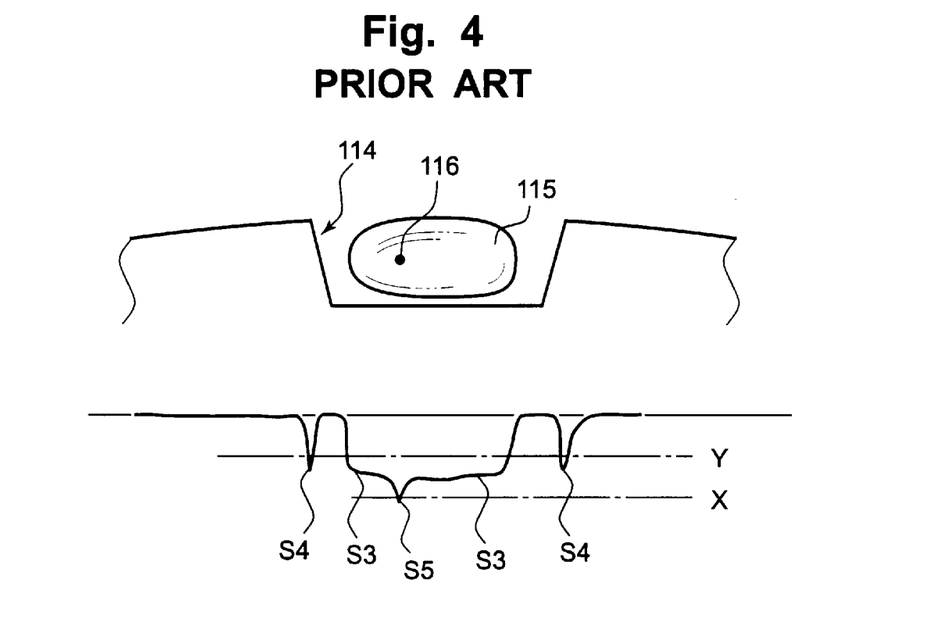
FIG. 4 is a diagram of reflection light signals of a grain in the conventional quality evaluation device.

In the case of a grain in which the reflection light diffuses, the reflection light having no relation to the quality is not detected from the grain being evaluated. However, as shown in FIGS. 3 and 4, depending on the shapes of a feeding means 112 which feeds the grain, it is possible that an edge portion 114 of the opening 113 (or recess) which holds the grain causes the occurrence of the reflection light which has no relation to the quality mentioned above. The signal waves of the reflection light received then is shown in FIG. 4. It can be appreciated therefrom that the reflection light from the edge portion 114 of the feeding means separate from the reflection light from the colored portion 116 of the grain 115 is detected as the reflection light similarly as the reflection light from the colored portion 116 of the grain. That is, since the signal S4 based on the reflection light from the edge portion is detected as a signal of the same level as that of the signal S3 based on the reflection light which depends on the shape of the grain, it is not possible to evaluate the shape of the grain by the reflection light, even though the colored portion itself is detected by the signal S5 based on the colored portion by providing two threshold values.

Thus, since the quality evaluation including the shape of the grain cannot be effected at the stage where the feeding of grains is made one by one by the feeding means, the device of this kind is separately provided, in addition to the feeding means having an edge portion for feeding the grains one by one, with a disk which has recesses for feeding the grains and which enables the shape evaluation without being influenced by the edge portion. In the device of this kind, it was essential to provide separately the feeding means for feeding the grains one by one and the evaluating means for evaluating the grains fed one by one. Also, since the grain and the edge portion could not be distinguished from each other only by the feeding means as explained above, it was not possible to specify the shape of the grain.

SUMMARY OF THE INVENTION

Thus, an object of the present invention is to provide a quality evaluation device which, without requiring any special devices, enables the accurate evaluation of pellet being transparent and having colored portions, and which enables the accurate counting of the number of granular objects one by one.

In the case of a grain in which the reflection light diffuses, since the light which influences the quality evaluation is not the reflection light from the grains being evaluated but is the reflection light from the edge portion of the feeding means, the conventional arrangement had to have the feeding means and the evaluating means as two separate means. According to the present invention, however, these means are unitarily constructed, thus providing a quality evaluation device for granular objects at a low cost.

The present invention provides a granular object evaluation device for the evaluation of quality and shapes of transparent or translucent granular objects, the device comprising:

a feeding means which feeds an individual granular object into a measuring area;

an illuminating means which irradiates light to the granular object fed into the measuring area by the feeding means;

a detecting means in which a detection viewing line is directed to the measuring area through a center portion of the illuminating means and which receives reflection light from the granular object located at the measuring area;

a light shielding plate which, for preventing the light from the illuminating means from directly incident on the detecting means, is located between the light illuminating means and the detecting means, and has an opening through which the detection viewing line passes;

a control means which analyses detected signals from the detecting means and evaluates quality and shapes of the granular object; and a shielding mask which shields light from a predetermined area such that no irradiation is made directly on the granular object from the predetermined area of the illuminating means with the detection viewing line being in the center thereof.

By experiment, the inventors of the present invention have found that, where a part of the illuminating means with the viewing line being in the center thereof is shielded so that the light from a predetermined radius of the illuminating means with the center thereof being the viewing line of the detecting means which receives the quantity of the light reflected from the granular object does not directly illuminate the granular object, the influence of the reflection light, which has no relation to the quality evaluation, other than the reflection light from a colored portion of the object being evaluated is reduced. That is, in this way, the reflection light from the end face of the transparent pellet, which was received as representing a dark portion in the conventional arrangement, is now received as comparatively light reflection light, and also the reflection light from the edge portion of the grain feeding means is now received as comparatively weak beams of reflection light so that any possibility for the reflection light to give adverse influence to the signal at the receiving section has become extremely small. Thus, even when the pellet as the object to be evaluated is transparent, or even when the feeding means for grains has an edge portion, the quality evaluation of the granular object having, for example, a colored portion can now be carried out very easily.

By providing two kinds of threshold values, namely, the first threshold value for obtaining signals of the start end and the finish end of a granular object from the quantity of the light reflected and the second threshold value for obtaining signals of the colored portion, it is enabled to obtain the signals for the lengths for evaluating the quality of the granular object or the signals for evaluating the colored portion. Since the present invention has made it possible to eliminate the influence from the end faces of the granular object and the influence from the edge portion of the feeding means, it has become easy to distinguish the end faces of the granular object and easy to obtain the information concerning the shapes, particularly, the lengths. By evaluating the start end and the finish end of the granular object, it is made possible, through the evaluation of the signal of the color portion between them, to obtain the information concerning the size of the colored portion.

As already explained, the experiment has proven that, where a portion of the illuminating means with the center thereof being the viewing line is masked by the shielding mask, the influence from the reflection light having no relation to the quality evaluation other than the reflection light from the object being evaluated is reduced. Thus, according to the present invention, the object is achieved by a simple means wherein the illuminating means is constructed by providing a plurality of light illuminating sources, of which two light illuminating sources are arranged such that the viewing line of the light receiving section is positioned between two parallel fluorescent lamps, and a part of the fluorescent lamps within a predetermined radius with its center being the viewing line is shielded.

The device according to the present invention includes a first comparing section in which the first threshold value for obtaining signals of the start end and the finish end of a granular object is set, and a second comparing section in which the second threshold value for evaluating the colored portion of the granular object is set. According to the invention, since the influence from the end faces of the granular object and the edge portion of the feeding means has been eliminated, the first comparing section having the threshold value is provided for evaluating the start end signal and the finish end signal and, since the start end signal and the finish end signal can be output at these comparing sections, the control section may receive these signals as those indicating the shapes of the granular objects and may calculate the lengths and sizes thereof. Also, the second comparing section having the second threshold value is separately provided. At this second comparing section, the colored portion signal can be output so that the control section may receive these signals as those indicating the colored portion and may calculate the size of the colored portion.

In the quality evaluation device according to the present invention, the two sets of light receiving means in each of which the light source, the light receiving section, and the light shielding plate are unitarily formed, may be arranged such that they are disposed symmetric with each other with respect to the center of the locus of the movement of the granular object, the viewing point of the light receiving section of one of the light receiving means faces over the shielding mask of the other light receiving means, the viewing point of the light receiving section of the other light receiving means faces over the shielding mask of one of the light receiving means, and the opening is provided on the shielding mask on the viewing point.

In the device as arranged above, a part of the shielding mask which becomes the viewing point is opened and a part of the light source is exposed so that the light receiving means which are symmetric with each other plays the role of the color plate (background) in addition to the role of the light shielding mask. Especially the light illuminating source which is constituted by, for example, fluorescent lamps which are like bars and have circular sections can be effectively utilized for the realization of the device.

In the quality evaluation device of the present invention, the shielding cover is provided to cover around the light source concentrically with the circularly formed shielding mask, and the illuminating portion of the illuminating means is arranged in a donut form with the center of the viewing line being in the center thereof, and it has been proven by experiments that this arrangement has made it possible to achieve a further reduction in the influence of the reflection light that may be caused by the reflection light from the end faces of the transparent pellet or from the edge portion of the grain feeding means.

Where, by the scanning at the light receiving section, the quality evaluation device for the granular objects eliminates the influence of the reflection light having no relation to the quality, the reflection signal from the end faces of the transparent pellet can be utilized as a signal for detecting the length of the pellet. This means that this device can count the number of granular objects so that the evaluation of the transparent or translucent pellet and the counting of the granular objects can be performed simultaneously. Also, when the device is used for the grains, it is possible to take-in the information for evaluating the quality of the grains, which enables the great reduction in the size of the device.

BRIEF DESCRIPTION OF THE DRAWINGS

The above and other objects, features and advantages of the present invention will be apparent from the following description of the preferred embodiment of the invention explained with reference to the accompanying drawings, in which.

PREFERRED EMBODIMENTS OF THE INVENTION

Now, a preferred embodiment of the quality evaluation device according to the invention is explained with reference to FIGS. 5 to 7.

Figure 5:
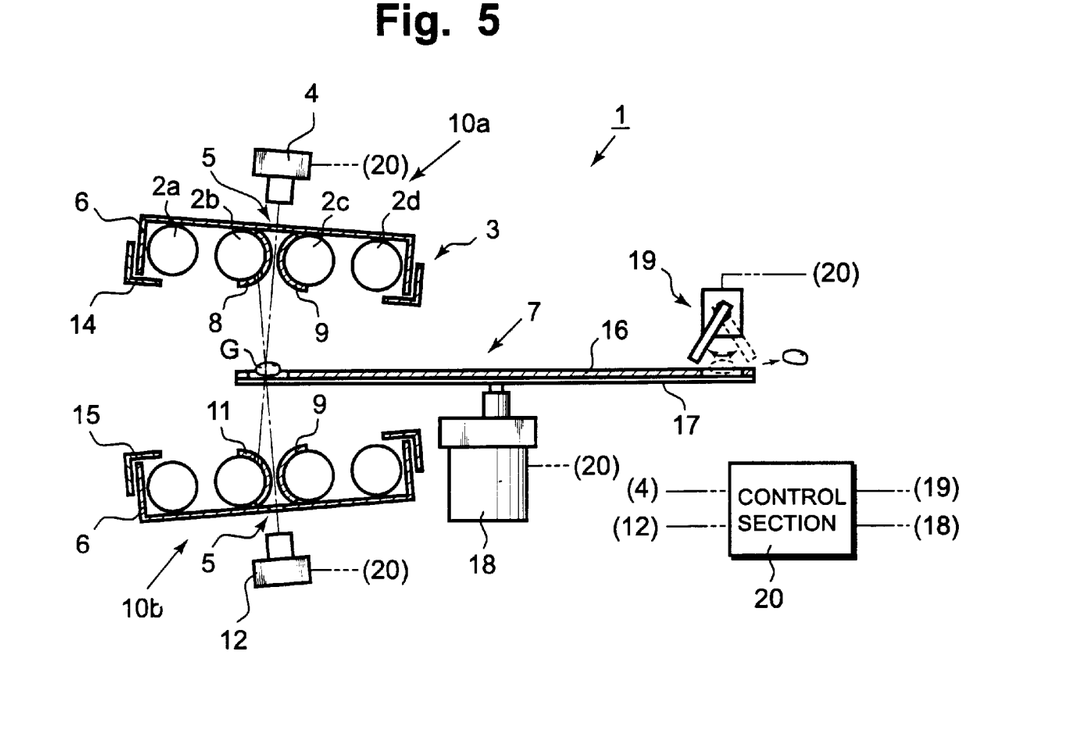
FIG. 5 is a sectional view of main elements of a quality evaluation device according to the present invention.

As shown in FIG. 5, the quality evaluation device 1 has the illuminating means, that is, a light source 3 equipped with straight tube type fluorescent lamps 2a–2d which constitute a plurality of light illuminating sources arranged in four parallel lines, of which two middle fluorescent lamps 2b and 2c are arranged such that the viewing line is disposed between them, a plurality of light receiving sections 4, 12 equipped with a converging lens 4a, a light receiving sensor 4b and an amplifier 4c (FIG. 7), a light shielding plate 6 having an opening 5 for passing the viewing line and disposed between the illuminating means 3 and the light receiving section 4 (12), and a feeding section 7 which rotates and feeds a granular object to the viewing line passing through the opening 5 of the light shielding plate 6 and between the fluorescent lamps 2b, 2c.

Figure 6:
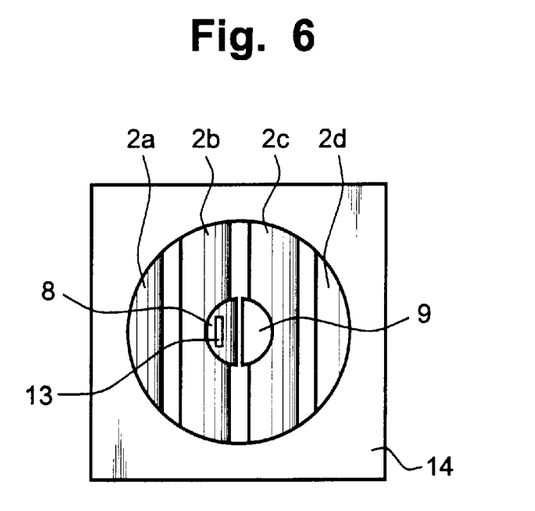
FIG. 6 is a plan view of a light source of the quality evaluation device according to the present invention, as viewed from a granular object side.
Figure 7:
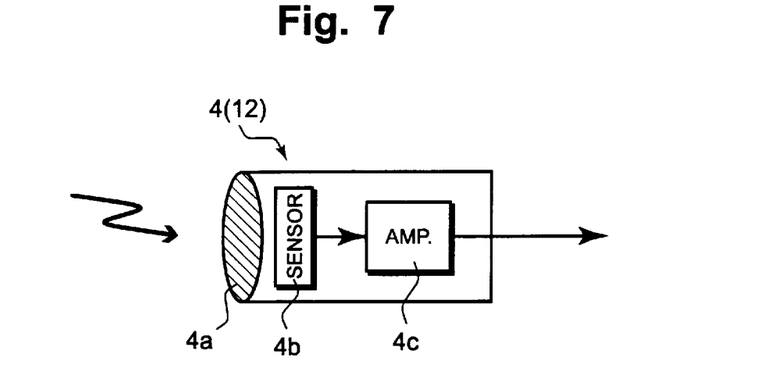
FIG. 7 is a diagram for showing a structure of the light receiving section in the device according to the present invention.

In the device constructed as above, FIG. 6 shows a state of the light source 3 as viewed from a granular object side.

As shown in FIG. 6, as a feature of the present invention, a part of the light source with the viewing line being in the center is shielded by circularly formed shielding masks 8, 9 so as to prevent the direct irradiation, on the granular object, of the light of the fluorescent lamps 2b, 2c existing within a predetermined radius, with the viewing line being in its center, of the light receiving section 4 which receives the quantity of the reflection light from the granular object G. In this way, any beams of light to irradiate the granular object substantially parallel to the viewing line become none.

Further, the two sets of the light receiving units, one being the light receiving unit 10a formed as a unit by the light source 3, the light receiving section 4 and the light shielding plate 6 and the other being the light receiving unit 10b formed as a unit by the light source 3, the light receiving section 12 and the light shielding plate 6, are arranged symmetric with each other with respect to the center of the moving locus of the granular object G. The viewing point of the light receiving section 4 faces over the shielding mask 11 and the viewing point of the light receiving section 12 faces over the shielding mask 8. Each of the shielding masks 8, 11 on the viewing line is provided with an opening 13. Also, according to the invention, the light source 3 is provided with shielding cover 14 (15) to cover around the light source in such a way that the cover is concentric with each of the circularly formed shielding masks 8, 9 (9, 11). Thus, the illuminating portion of the light source is in a donut shape with the viewing line in the center.

The feeding section 7 is provided around a disk 16 with a plurality of recesses each of which is adapted to hold the granular object and a bottom surface of the recess is provided with a bottom plate 17 made of a transparent material. Also, this disk 16 is provided at its center with a driving means 18 for decelerated driving. A sorting section 19 may be disposed at a location different from the location of the viewing point on the light receiving section 4 on the disk 16.

Further, the device according to the invention is equipped with a control section 20 which analyses the signals received from the light receiving sections 4, 12 and evaluates the quality and shapes of the granular object. The control section 20 outputs driving signals to the driving means 18 and the sorting section 19.

Figure 8:
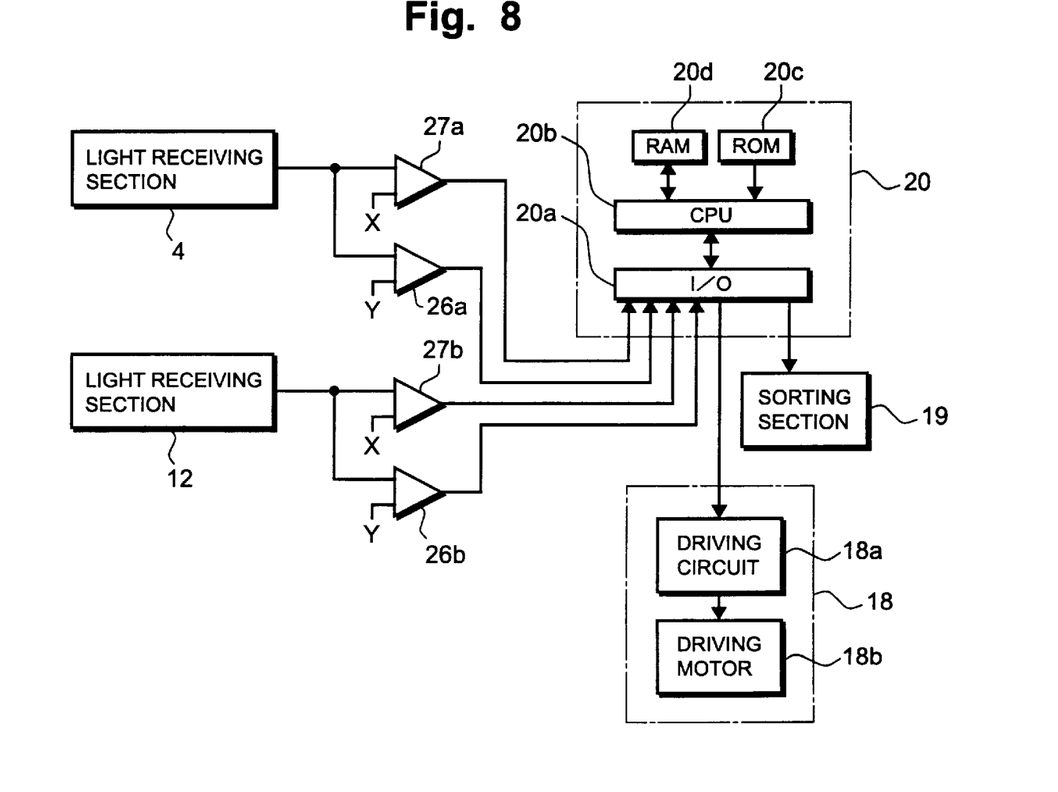
FIG. 8 is a block diagram for showing a relation between a control section and light receiving and sorting sections in the device according to the present invention.

Now, the control section 20 and the driving section 4, 12, and the driving means 18 and the sorting section 19 are explained with reference to FIG. 8. The signals received from the light receiving section 4 (12) are input into comparators 26a, 26b in which is set the threshold value Y for evaluating the signals representing the start end and the finish end of the granular object, and into comparators 27a, 27b in which is set the threshold value X for evaluating a colored portion of the granular object. The signals from the comparators 26a, 26b, 27a, 27b are input into an I/O port 20a of the control section 20. The driving means 18 is connected to the I/O port 20a. The driving means 18 is constituted by a driving circuit 18a and a driving motor 18b connected to the driving circuit 18a.

The signals from the light receiving sections 4, 12 are compared respectively with the threshold values X, Y by the comparators 26a, 26b, 27a, 27b. If the light receiving signal exceeds each of the threshold values, an ON (1) signal is output to the I/O 20a. If the light receiving signal does not exceed each of the threshold values, an OFF (0) signal is output. The CPU 20b of the control means 20 repeats a series of steps by sequentially and repeatedly detecting the outputs of the comparators 26a, 27a based on the signals from the light receiving section 4 and the outputs of the comparators 26b, 27b based on the signals from the light receiving section 12 according to the procedure stored in a ROM 20c, and performing calculation based on the detected signals and evaluation of quality, and the results thereof are stored in a RAM 20d. Also, based on the quality evaluation, a sorting signal of the granular object is output to the sorting section 19 through the I/O port 20a. Based on this signal, the sorting section 19 performs predetermined steps. The actual performance in the sorting section 19 is such that, for the performance to be delayed for a predetermined time from the generation of the sorting signal, a delay circuit (not shown) may be provided in the control section 20 or in the sorting section 19, and the time delay caused by the locations of the light receiving sections 4, 12 and the sorting section 19 may be compensated.

Figure 9:
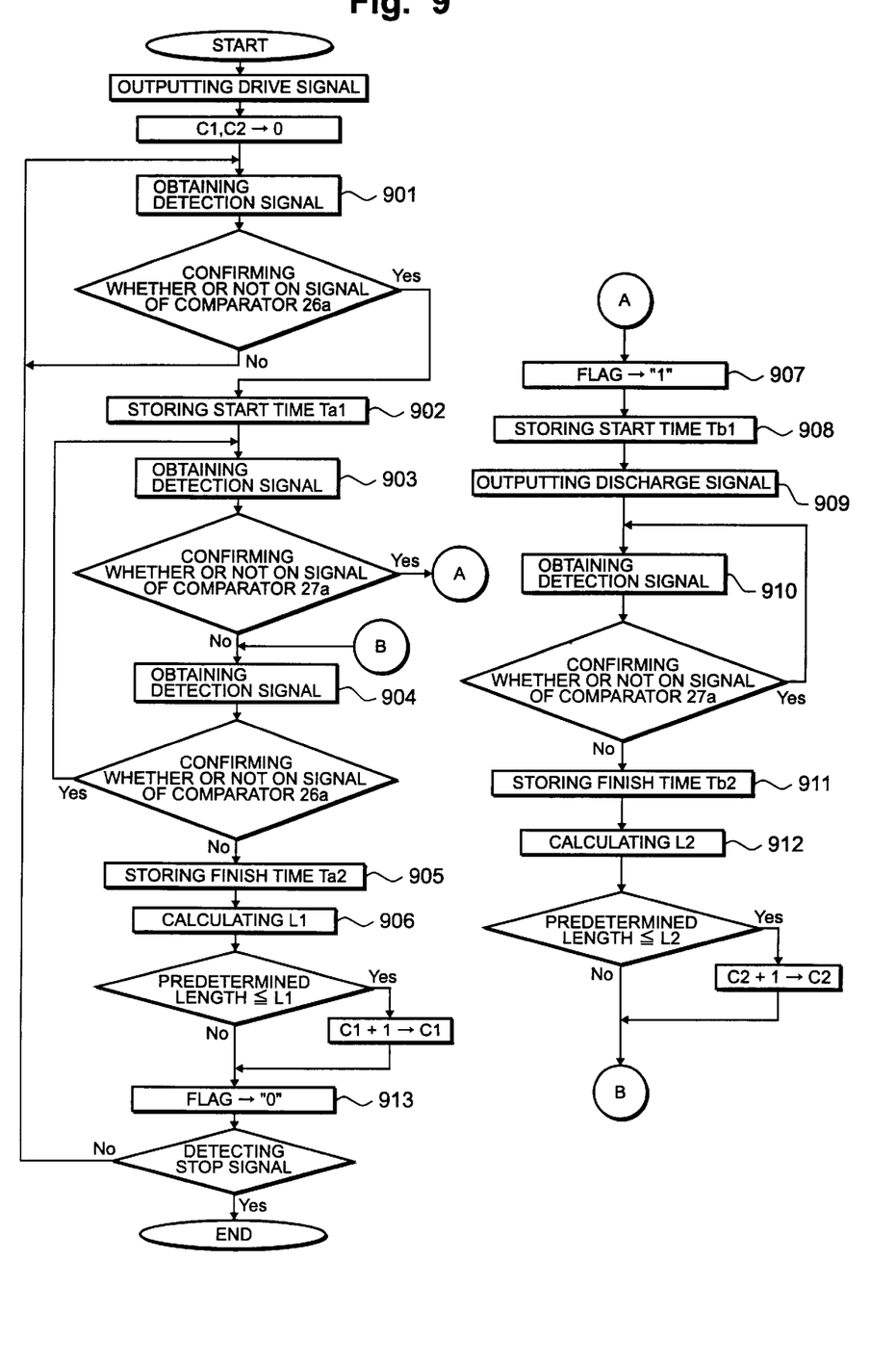
FIG. 9 is a diagram for showing steps for processing signals stored in ROM.

In a ROM 20c of the control section 20, a signal processing program such as that shown in FIG. 9 is stored, and is executed by start instructions. With reference to FIG. 9, the procedure for processing the light receiving signal from the light receiving section 4 is explained. Explanation is omitted for the processing of the light receiving signal from the light receiving section 12 since the processing is the same as that for the light receiving section 4. First, with the start, the drive signal is output to the driving circuit 18a of the driving means 18, the driving motor 18b starts, and the feeding means 7 starts to rotate. Then, count 0 is stored in counts C1, C2 of the RAM 20d. This count is for counting the number of granular objects on a quality to quality basis, such as "non-defective" or "defective" which is predetermined. The detection signal is obtained from the I/O port 20a (step 901), and the presence or non-presence of the ON signal of the comparator 26a is confirmed. This confirmation is repeated until the ON signal of the comparator 26a is input.

When the ON signal of the comparator 26a is confirmed, the RAM 20d stores T$a$1 as the start end of the granular object (step 902), and as the time when the confirmation is started. Then, the detection signal is obtained from the I/O port 20a and whether the ON signal of the comparator 27a is present is confirmed. If the signal from the comparator 27a is OFF signal, the detection signal indicative of, for example, no presence of a color portion is obtained from the I/O port 20a (step 904), thus confirming whether or not the ON signal of the comparator 26a is present. Here, when the ON signal is detected, the detection signal is obtained again from the I/O port 20a (step 903), thus confirming whether or not the ON signal of the comparator 27a is present. In the absence of the ON signal from the comparator 27a, the confirmation is repeated for the ON signal of the comparator 26a and the comparator 27a.

After the above is repeated, when the OFF signal of the comparator 26a is confirmed, the RAM 20d stores T$a$2 as the finish end of the granular object, that is, the time when the confirmation is finished (step 905). From the time started T$a$1 and the time finished T$a$2 as well as the moving speed stored in advance in the ROM 20c, the CPU 20b calculates the length L1 of the granular object (step 906), and this length L1 is compared with a predetermined length stored in advance in the ROM 20c, and if the former is larger than the latter, the count C1 is incremented by 1 as a standard granular object. Here, it is possible to set a plurality of the predetermined lengths, hence a plurality of groups of the predetermined lengths, and the counting may be made on a group to group basis.

While the confirmation of the presence of the ON signal of the comparator 26a and the comparator 27a is repeated after the detection signal is obtained from the I/O port 20a (steps 903, 904), when the presence of the ON signal of the comparator 27a is confirmed as indicating the colored portion, a flag which indicates whether or not there is a colored portion is assigned to the RAM 20d is made "1" (step 907), and the RAM 20d stores T$a$1 as the time when the confirmation is started (step 908). Also, when the signal of the comparator 27a has been confirmed, a discharge signal is output to the sorting section 19 (step 909). Further, the detection signal is obtained from the I/O port 20a (step 910), and the detection of the ON signal of the comparator 27a is repeated, and when the change to the OFF signal takes place, the RAM 20d stores T$b$2 as the time when the confirmation is finished (step 911). From the time started T$a$1 and the time finished T$a$2 as well as the moving speed stored in advance in the ROM 20c, the CPU 20b calculates the length (size) L2 of the colored portion (step 912), and this length L2 is compared with a predetermined length stored in advance in the ROM 20c, and if the former is larger than the latter, the count C2 is incremented by 1 as the colored portion being large. Here, it is possible to set a plurality of the predetermined lengths, hence a plurality of groups of the predetermined lengths, and the counting may be made on a group to group basis.

When the counting is completed, the signals from the comparator 26a and the comparator 27a are again obtained from the I/O port 20a and the ON signal is repeatedly confirmed (steps 903, 904) and, when the OFF signal of the comparator 26a is repeatedly confirmed, the RAM 20d stores T$a$2 as the finish end signal, that is, the time when the confirmation is finished (step 905), and the CPU 20b calculates the length L1 of the granular object with the colored portion from the moving speed stored in advance in the RAM 20c (step 906), and if this length L1 is larger than the predetermined length stored in advance in the ROM 20c, the count C1 is incremented by 1 as the standard granular object. Here, since the flag of the RAM 20d is already "1", the counting is not made at the C1 but may be counted at the colored portion division, for example, as the C3. In this case, it is necessary that the C3 be set in advance in the RAM 20d. Also, it is possible that the length L2 of the colored portion and the L1 of the granular object are counted in a combined division. After the counting, the flag which indicates whether or not there is a colored portion is assigned to the RAM 20d is made "0" (step 913), and the new measuring cycle starts. The division of the granular object can be determined through a plurality of steps by the length or the size of the colored portion in the case of, for example, pellets. However, in the evaluation device such as according to the present invention in which the elimination is made of the influence of the reflection light from the end faces of, for example, pellet and the reflection light from the edge portion of the feeding means which are unnecessary for the evaluation of the granular objects, it is possible to set further evaluation divisions by providing the color signal to be obtained from a color image pick-up element and the threshold values individually for the particular colors necessary for the evaluation.

Figure 10A:
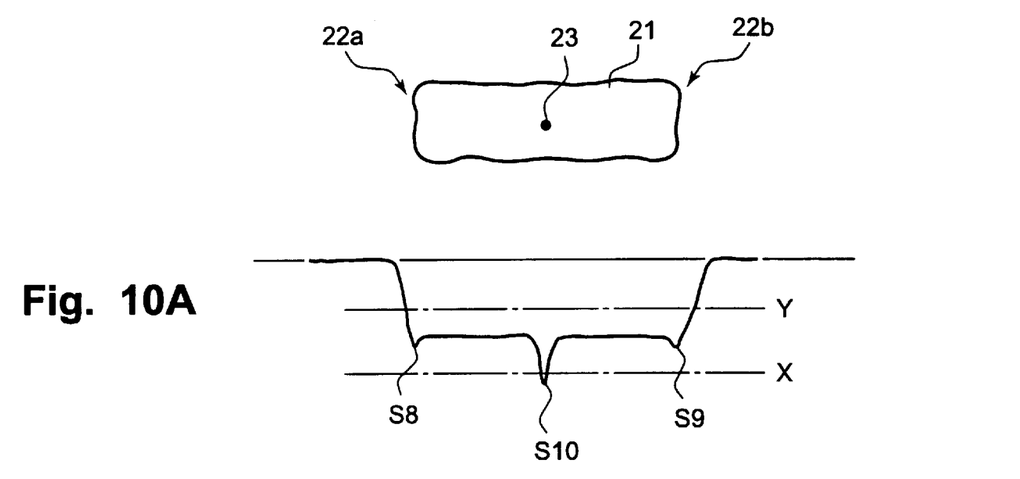
FIGS. 10A and 10B are diagrams for showing reflection light signals when the present invention is applied to a transparent pellet.
Figure 10B:
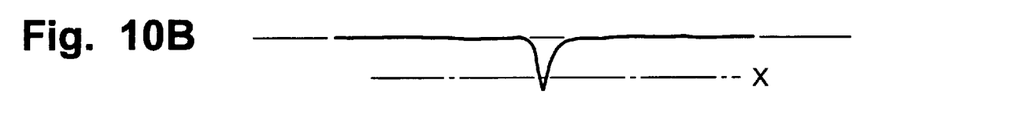

FIGS. 10A and 10B show the signals obtained when the measuring is made of the reflection light from the transparent pellet 21 in the arrangement as explained above. According to the signal waves of FIG. 10A, although the signals S8, S9 caused by the influenced of the end faces 22a, 22b of the transparent pellet are seen, the level thereof is clearly distinguished from that of the signal S10 caused by the colored portion 23 so that the provision of the threshold value X will enable the evaluation of the colored portion 23. Further, whereas the reflection light from the end faces 22a, 22b in the conventional device was an obstacle in the quality evaluation, the device according to the present invention enables the detection as the end faces 22a, 22b so that, by the provision of the threshold value Y, the front end and the rear end of one pellet can be recognized even when such pellet is transparent and this ensures the accurate detection of one pellet. That is, it has become possible to make the counting of granular objects, which is essential in the quality evaluation.

The signal waves shown in FIG. 10B are of a signal when only one of the light receiving units 10a, 10b is provided and the background is not provided. Since the pellet is transparent, no reflection light is detected other than from the colored portion 23. No reflection light comes from the end faces either, so that the colored portion 23 is accurately detected by the provision of one threshold value X.

As already explained, the experiment has proven that, the shielding of a part of the fluorescent lamps 2b, 2c with the viewing line being in the center, makes it possible that the light of the fluorescent lamps 2b, 2c within the predetermined radius, with the viewing line being in the center, of the light receiving section 4 (12) which receives the quantity of the reflection light from granular object G, is prevented from directly irradiating the granular object, and the influence of the reflection light other than from the colored portion of the object, which has no relation to the quality evaluation, is reduced. That is, the reflection light from the end faces of the transparent pellet which was received as a dark portion in the conventional device is now received as comparatively light reflection light so that the distinction from the colored portion has become clear and any adverse influence to the signal at the light receiving section has become extremely small.

Figure 11A:
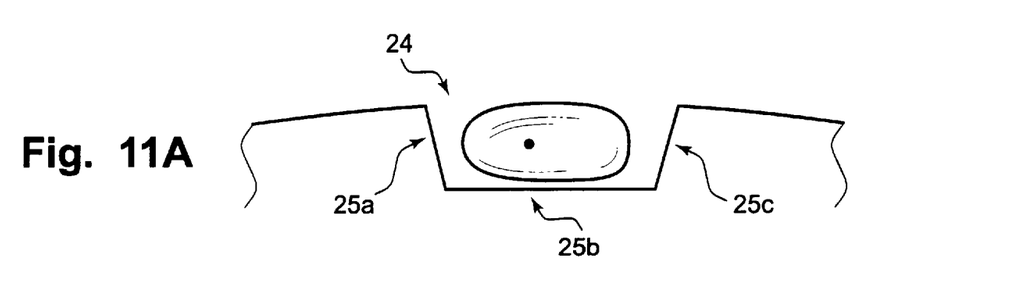
FIGS. 11A and 11B are diagrams for showing reflection light signals when the present invention is applied to a grain.
Figure 11B:
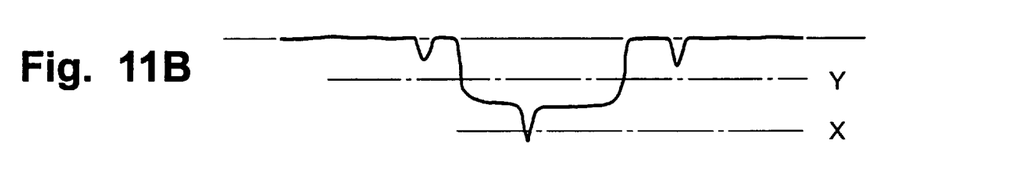
Figure 12:
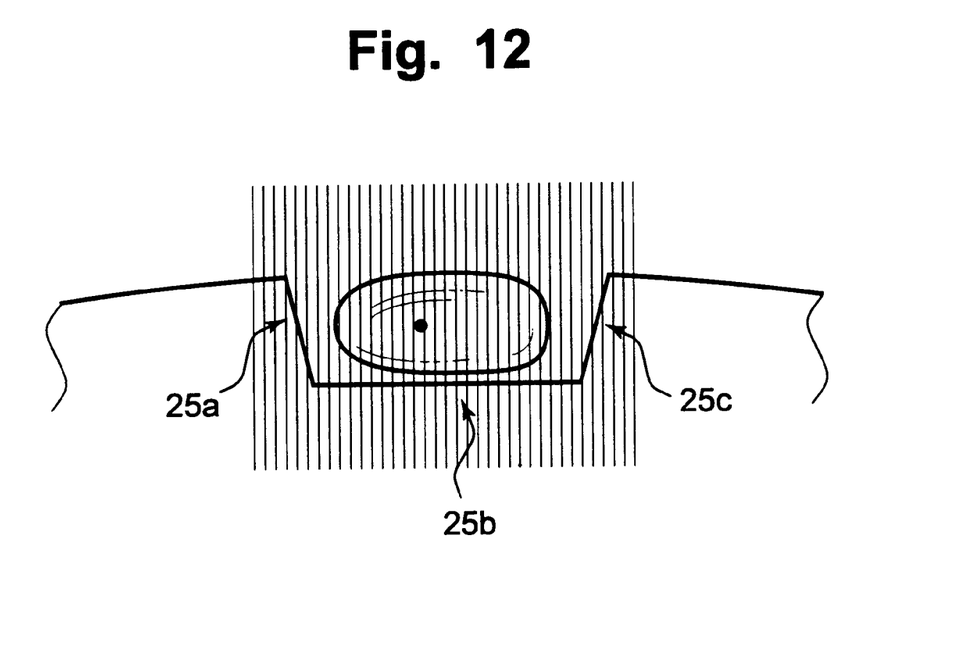
FIG. 12 is diagram for showing a scanning state when the present invention is applied to a grain.

Next, among the granular objects, the application especially to a rice grain is explained based on FIGS. 11A, 11B and FIG. 12. For measuring the reflection light of grains in the arrangement as explained above, the periphery of the feeding section shown by the numeral 7 in FIG. 5 is provided with openings 24 instead of the recesses for feeding the grains. In the conventional device, the signal of the reflection light from the edge portions 25a, 25b, 25c of the openings 24 was the same as the signal from the grain itself. However, as shown in FIG. 11B, the reflection light from the edge portions in the grain feeding means in the device according to the present invention is received as comparatively light reflection light or weak reflection light so that any adverse influence to the signal at the light receiving sections 4, 12 has become extremely small. That is, even in the case of grains, the two threshold values may be set and the evaluation as to hues of the colored portion may be made by the threshold value X. The threshold value Y which is set independent of the signal of the edge portions 25a, 25b, 25c may be used to detect the shapes of the grains.

What the above means is that, even with the device having a feeding means equipped with a conventional opening section, the detection of the hue of grains and one grain at a time can be made reliably without having influence from the edge portion of the opening so that the device does not require any special disk means. That is, the feeding means 7 as shown in FIG. 5 may simply be a means having the opening 24 which has the edge portion or, since the application of the invention enables the analysis of the grains while the direct sampling of the grains is being performed with the feeding means 7 being inclined and since it is not necessary, unlike in the convention device, to provide separately the feeding means which enables the evaluation in the evaluation device and the feeding section which, though the evaluation cannot be made, enables the feeding and counting of one grain at a time, the size of the device can be reduced significantly.

Further, as seen in FIG. 12, for analyzing shapes of a grain, a means such as CCD sensor is incorporated in the light receiving section 4 and, by obtaining the light quantity signal of the reflection light through the scanning signals, the shapes of the grain can accurately be determined. The evaluation of shapes of the grain is thus facilitated because, in the absence of any influence from the edge portions 25a, 25b, 25c of the opening 24, the boundary lines between the edge portion 25a and the grain, between the edge portion 25b and the grain, and between the edge portion 25c and the grain can respectively be determined for sure by the signals obtained by scanning. That is, the light reflected from the edge portion of the feeding section is received as comparatively weak reflection light as compared with the reflection light from the grain, and thus any adverse influence to the signal of the light receiving section is extremely small.

The embodiment of the invention explained above relates to the arrangement in which the illuminating means is constituted by the straight tube type fluorescent lamps, but a plurality of ring type fluorescent lamps may instead be provided concentrically with the viewing line being in the center. Also, the light source is not limited to the use of the fluorescent lamps as it may employ a plurality of incandescent lamps. Further, the light source may well be a surface illuminant. That is, any light source will do provided that such light source is one in which the direct beams of light of the illuminating means do not directly irradiate the granular objects.

The advantages achieved by the present invention include the following. Since the light reflected from the end faces of the transparent pellet, or the light reflected from the edge portion of the grain feeding means is received as comparatively light reflection light or as comparatively weak reflection light, any adverse effect to the signal at the light receiving section has become extremely small. Thus, whether the object being measured is a transparent pellet, or whether or not there is an edge portion in the feeding means for grains, the quality evaluation of granular objects having colored portions has become extremely easy.

Since the reflection light which becomes an obstacle in the quality evaluation is reduced, the provision of the evaluating means having the first threshold value for determining the start end and the finish end of the granular object by detecting the reflection light from the end faces thereof, and of the evaluating means having the second threshold value for determining the colored portion of the granular object, has made it easy to count the number of objects and to evaluate the colored portions. As a result, the evaluation of the colored portion of the transparent pellet, which was difficult in the conventional device, has become possible, and the application can be made even to the feeding means having the edge portion that reflects.

By a simple means according to the invention in which the viewing line of the light receiving section is positioned between the two light illuminating sources, for example, the two fluorescent lamps arranged in parallel, and a portion of the fluorescent lamps within a predetermined radius with the viewing line being in the center is shielded, it has become possible to receive the light reflected from the end faces of the transparent pellet or the light reflected from the edge portion of the feeding means as comparatively light reflection light or comparatively weak reflection light, thus enabling the easy and accurate evaluation of the granular objects.

According to the invention, each of the shielding masks of the symmetrically arranged respective light receiving means plays, in addition to the role of the shielding masks, the role of a color plate (background) formed by opening a part of the shielding mask for the viewing line so as to have a part of the light source exposed. Consequently, the color plate (background), which was separately provided in the conventional device, is dispensed with, and this enables the unitary construction of the device with the reduced number of elements or parts.

Since the light source is formed in a donut form, any influence of the reflection light from the end faces of the transparent pellet or from the edge portion of the feeding means for the grain is further reduced.

By the scanning through the light receiving section, the reflection light from the end faces of the transparent pellet can be utilized as the signal representing the length of the transparent pellet. As a result, according to the invention, since the number of granular objects can be counted, the quality evaluation of the transparent or translucent pellet and the counting of the number can be carried out simultaneously. Likewise, when the invention is applied to grains and, even when the measuring is made by the feeding means as in the conventional device, it is possible to evaluate not only the colored portion of the grain but also the shapes of the grain.

While the invention has been described in its preferred embodiment, it is to be understood that the words which have been used are words of description rather than limitation and that changes within the purview of the appended claims may be made without departing from the true scope of the invention as defined by the claims.

What is claimed is:

1. A granular object evaluation device which evaluates a quality and a shape of a transparent or translucent granular object, the device comprising:

a feeding means which feeds an individual granular object into a measuring area;

a detecting means in which a detection viewing line is directed to said measuring area and which receives reflected light from the granular object located at said measuring area;

an illuminating means which is located between said detecting means and said measuring area, has a center area through which said detection viewing line passes, and irradiates light to the granular object fed into said measuring area by said feeding means;

a light shielding plate which is located between said illuminating means and said detecting means, prevents the light from said illuminating means from being directly incident on said detecting means, and has an opening through which said detection viewing line passes;

a shielding mask which is arranged with said detection viewing line as the center and which covers a predetermined area of said illuminating means with said detection viewing line as the center so that light that is parallel to the detection viewing line and emitted from said illuminating means at said predetermined area is prevented from being directly incident on the granular object; and a control means which analyzes detected signals from said detecting means and evaluates the quality and the shape of the granular object.

2. A granular object evaluation device according to claim 1, in which said illuminating means comprises a plurality of fluorescent lamps of a straight tube type arranged in a plurality of lines, said detection viewing line of said detecting means passing through between predetermined two fluorescent lamps among said plurality of fluorescent lamps.

3. A granular object evaluation device according to claim 1, in which said detecting means comprises a first comparator provided with a first threshold value for evaluating a start end and a finish end of the granular object, and a second comparator provided with a second threshold value for evaluating a colored portion of the granular object.

4. A granular object evaluation device according to claim 1, which is provided with first and second light receiving assemblies each comprising said illuminating means, said detecting means, said light shielding plate and said shielding mask having an opening exposing said illuminating means, said first and second light receiving assemblies being arranged symmetric with each other with a measuring area being in the center, said detection viewing line of said first light receiving assembly facing said opening of said shielding mask of said second light receiving assembly, and said detection viewing line of said second light receiving assembly being directed towards said opening of said shielding mask of said first light receiving assembly.

5. A granular object evaluation device according to claim 1, which further comprises a shielding cover to cover around said illuminating means concentrically with said shielding mask which is circularly formed.

6. A granular object evaluation device according to claim 1, in which said detecting means has a CCD and said reflection light from the granular object is received through scanning by said CCD.

* * * * *